US007235685B2

(12) United States Patent
Rajagopalan et al.

(10) Patent No.: US 7,235,685 B2
(45) Date of Patent: Jun. 26, 2007

(54) AROMATIC SULFENATES FOR TYPE I PHOTOTHERAPY

(75) Inventors: Raghavan Rajagopalan, Beechwood, OH (US); Gary L. Cantrell, Troy, IL (US); Samuel I. Achilefu, St. Louis, MO (US); Joseph E. Bugaj, St. Charles, MO (US); Richard B. Dorshow, St. Louis, MO (US)

(73) Assignee: Mallinckrodt, Inc., St. Louis, MO (US)

( * ) Notice: Subject to any disclaimer, the term of this patent is extended or adjusted under 35 U.S.C. 154(b) by 214 days.

(21) Appl. No.: 09/898,887

(22) Filed: Jul. 3, 2001

(65) Prior Publication Data

US 2003/0158127 A1 Aug. 21, 2003

(51) Int. Cl.
*C07K 313/08* (2006.01)

(52) U.S. Cl. .................. 558/62; 514/418; 604/20; 606/2; 607/88; 607/89

(58) Field of Classification Search ............... 530/324, 530/399; 606/2; 604/20; 607/88, 89; 514/418; 558/62

See application file for complete search history.

(56) References Cited

U.S. PATENT DOCUMENTS

| 5,518,888 | A | 5/1996 | Waldman ................ 435/7.23 |
| 5,650,292 | A | 7/1997 | Scherz et al. ............. 435/68.1 |
| 5,714,342 | A | 2/1998 | Komoriya et al. .......... 435/23 |
| 6,462,070 | B1 | 10/2002 | Hasan et al. ............... 514/410 |

OTHER PUBLICATIONS

Hillemanns, P. (International Journal of Cancer. Journal international du cancer, 81 (1) 34_8, 1999).*
Li W. (Journal of photochemistry and photobiology. B, Biology 60 (2□3) 79-86, 2001).*
Vaupel P (Strahlentherapie und Onkologie : Organ der Deutschen Rontgengesellschaft 174 Suppl 4 6-12, 1998).*
Anderson, Gregory S. (Journal of photochemistry and photobiology. B, Biology 68, (2-3) 101-8 2002).*
Grossweiner L. I. (Photochemistry and photobiology 46 (5) 911-7, 1987).*
Pope A.J. (Journal of urology 145 (5) 1064-70, 1991).*
Gluckman J. L. (Laryngoscope 101 (1 Pt 1) 36-42, 1991).*
Bonnett R., Journal of photochemistry and photobiology. B, Biology, (Jun. 1990) 6 (1 2) 29-37.*
Yates, Andrew (Bioorganic & Medicinal Chemistry Letters 15(16), 3758-62, 2005).*
S. Achilefu, Ph.D. et al., *Novel Receptor-Targeted Fluorescent Contrast Agents for In Vivo Tumor Imaging*, Investigative Radiology, vol. 35, No. 8, 2000, 479-485.
Jerome Amaudrut et al., *The Thermal Sulfenate-Sulfoxide Rearrangement: A Radical Pair Mechanism*, J. Amer. Chem, Soc. , vol. 122, 2000, 3367-3374.
A. Andreoni et al., *Tumour photosensitization by chemotherapeutic drugs*, Biology, N3, 1993, 43-46.

Byron Ballou et al., *Tumor labeling in vivo using cyanine-conjugated monoclonal antibodies*, Cancer Immunology and Immunotherapy, vol. 41, 1995, 257-263.
M.D. Daniell et al., *A History of Photodynamic Therapy*, Aust. N.Z. J. Surg., vol. 61, 1991, 340-348.
T.J. Dougherty et al., *Photoradiation Therapy. II. Cure of Animal Tumors with Hematoporphyrin and Light*, Journal of the National Cancer Institute, vol. 55, No. 1, 1975, 115-121.
G. Freiherr, *The Light Stuff: Optical Imaging in Medical Diagnosis*, Medical Device & Diagnositc Industry Magazine, 1998, 1-7.
M.R. Hamblin et al., *On the mechanism of the tumour-localising effect in photodynamic therapy*, J. Photochem. Photobiol. B: Biol., vol. 23, 1994, 3-8.
J. C. Hebden et al., *Diagnostic imaging with light*, The British Journal of Radiology, vol. 70, 1997, S206-S214.
D.J. Hnatowich et al., *Radioactive Labeling of Antibody: A Simple and Efficient Method*, Science, vol. 220, 1983, 613-615.
G. Jori, *Tumour photosensitizers: approaches to enhance the selectivity and efficiency of photodynamic therapy*, Journal of Photochemistry and Photobiology B: Biology, vol. 36, 1996, 87-93.
G. Jori, *Novel Therapeutic Modalities Based on Photosensitized Processes*, EPA Newsletter, No. 60, 1997, 12-18.
G. Jori, *Far-red-absorbing photosensitizers: their use in the photodynamic therapy of tumours*, J. Photochem. Photobiol. A: Chem., vol. 62, 1992, 371-378.
G. Jori et al., *Second Generation Photosensitizers for the Photodynamic Therapy of Tumours*, Light in Biology and Medicine, vol. 2, R.H. Douglas et al. (Eds.), 1991, 253-266.
M. Korbelik, *Photosensitizers in photodynamic therapy*, Periodicum Biologorum, vol. 93, No. 4, 1991, 563-574.
K. Licha et al., *New Contrast Agents for Optical Imaging: Acid-Cleavable Conjugates of Cyanine Dyes with Biomedicals*, Part of the SPIE Conference On Molecular Imaging: Reporters, Dyes, and Instrumentation, Proceedings of SPIE, vol. 3600, 1999, 29-35.
R.L. Lipson, M.D. et al., *Hematoporphyrin Derivative for Detection and Management of Cancer*, Cancer, vol. 20, No. 12, 1967, 2255-2257.
Y. Luo et al., *Rapid Initiation of Apoptosis by Photodynamic Therapy*, Photochemistry and Photobiology, vol. 63, No. 4, 1996, 528-534.
K. Matsumura, *1-Aminoacridine-4-carboxylic Acid*, Journal of the American Chemical Society, vol. 60, (1938) 591-593.
G.G. Miller et al., *Preclinical Assessment of Hypocrellin B and Hypocrellin B Derivatives as Sensitizers for Photodynamic Therapy of Cancer: Progress Update*, Photochemistry and Photobiology, vol. 65, No. 4, 1997, 714-722.
T. Parasassi et al., *Two-photon microscopy of aorta fibers shows proteolysis induced by LDL hydroperoxides*, Free Radical in Biology and Medicine, vol. 28, No. 11, 2000, 1589-1597.

(Continued)

*Primary Examiner*—David Lukton
(74) *Attorney, Agent, or Firm*—Wood, Herron & Evans, LLP (57) ABSTRACT

The present invention discloses novel sulfenate derivatives and their bioconjugates for phototherapy of tumors and other lesions. The sulfenates of the present invention are designed to absorb low-energy ultraviolet, visible, or near-infrared (NIR) region of the electromagnetic spectrum. The phototherapeutic effect is caused by direct interaction of free radicals, the reactive intermediate produced upon photofragmentation of the sulfenate moiety, with the tissue of interest.

17 Claims, 5 Drawing Sheets

OTHER PUBLICATIONS

D.J. Pasto et al., *Demonstration of the Synthetic Utility of the Generation of Alkoxy Radicals by the Proto-Induced, Homolytic Dissociation of Alkyl 4-Nitrobenzenesulfenates*, Tetrahedron Letters, vol. 35, No. 25, 1994, 4303-4306.

A. Pelegrin et al., *Photoimmunodiagnosis with antibody-fluorescein conjugates: in vitro and in vivo preclinical studies*, J. Cell Pharmacol, vol. 3, 1992, 141-145.

W. G. Roberts et al., *Role of Neovasculature and Vascular Permeability on the Tumor Retention of Photodynamic Agents*, Cancer Research, vol. 52, 1992, 924-930.

G.I. Stables et al., *Photodynamic therapy*, Cancer Treatment Reviews, vol. 21, 1995, 311-323.

T. Takemura et al., *Mechanism of Photodynamic Therapy: Exploration by Photophysiocochemical Study*, Frontiers of Photobiology, 1993, 503-506.

K.B. Trauner et al., *Photodynamic Synovectomy Using Benzoporphyrin Derivative in an Antigen-Induced Arthritis Model for Rheumatoid Arthritis.*, Photochemistry and Photobiology, vol. 67, No. 1, 1998, 133-139.

I.P.J. van Geel et al., *Photosensitizing Efficacy of MTHPC-PDT Compared to Photofrin-PDT in the RIF1 Mouse Tumour and Normal Skin*, Int. J. Cancer, vol. 60, 1995, 388-394.

EPO, *European Search Report*, EP Application No. 02744398.5—2177, PCT/US0219185, mailed on Jan. 1, 2006.

Pasto et al., *Photolysis of Alkyl 4-Nitrobenzenesulfenates. A New and Versatile Method for the Generation of Free Radicals*, J. Org. Chem. 1990, 55:5815-5816.

Petrovic et al., *Free Radical Phenylthio Group Transfer to Nonactivated g-Carbon Atom in the Photolysis Reactions of Alkyl Benzenesulfenates*, Tetrahedron Letters 38:7107-7110, 1997.

Phillips, *Chemical Mechanisms in Photodynamic Therapy with Phthalocyanines*, Prog. Reaction Kinetics, 22: 175-300, 1997.

PCT, *International Search Report*, PCT/US02/19185, Mailed on Jan. 23, 2003 (3 pages).

* cited by examiner

AROMATIC SULFENATES FOR TYPE I PHOTOTHERAPY

FIELD OF THE INVENTION

This invention relates to novel dye-sulfenate compositions and phototherapeutic procedures using these compositions.

BACKGROUND OF THE INVENTION

The use of visible and near-infrared (NIR) light in clinical practice is growing rapidly. Compounds absorbing or emitting in the visible or long-wavelength (UV-A, >350 nm) region of the electromagnetic spectrum are potentially useful for optical tomographic imaging, endoscopic visualization, and phototherapy. However, a major advantage of biomedical optics lies in its therapeutic potential. Phototherapy has been demonstrated to be a safe and effective procedure for the treatment of various surface lesions, both external and internal. Its efficacy is akin to radiotherapy, but it advantageously lacks the harmful radiotoxicity to critical non-target organs.

Phototherapy has been in existence for many centuries and has been used to treat various skin surface ailments. As early as 1400 B.C. in India, plant extracts (psoralens), in combination with sunlight, were used to treat vitiligo. In 1903, Von Tappeiner and Jesionek, used eosin as a photosensitizer for treating skin cancer, lupus of the skin, and condylomata of female genitalia. Over the years, the combination of psoralens and ultraviolet A (low-energy) radiation has been used to treat a wide variety of dermatological diseases and manifestations including psoriasis, parapsoriasis, cutaneous T-cell lymphoma, eczema, vitiligo, areata, and neonatal bilirubinemia. Although the potential of cancer phototherapy has been recognized since the early 1900s, systematic studies to demonstrate safety and efficacy began only in 1967 with the treatment of breast carcinoma. In 1975, Dougherty et al. conclusively established that long-term cure is possible with photodynamic therapy (PDT). Currently, phototherapeutic methods are also being investigated for the treatment of some cardiovascular disorders such as atherosclerosis and vascular restenosis, for the treatment of rheumatoid arthritis, and for the treatment of some inflammatory diseases such as Chron's disease.

Phototherapeutic procedures require photosensitizers (i.e. chromophores) having high absorptivity. These compounds should preferably be chemically inert and become activated only upon irradiation with light of an appropriate wavelength. Selective tissue injury can be induced with light when photosensitizers bind to the target tissues, either directly or through attachment to a bioactive carrier. Furthermore, if the photosensitizer is also a chemotherapeutic agent (e.g., anthracycline antitumor agents), then an enhanced therapeutic effect can be attained. The key requirements for the design of effective phototherapeutic agents are: (a) large molar extinction coefficients, (b) long triplet lifetimes, (c) high yields of singlet oxygen and/or other reactive intermediates, viz., free radicals, nitrenes, carbenes, or open-shell ionic species such as carbonium ions and the like, (d) efficient energy or electron transfer to cellular components, (e) low tendency to form aggregation in an aqueous milieu, (f) efficient and selective targeting of lesions, (g) rapid clearance from the blood and non-target tissues, (h) low systemic toxicity, and (i) lack of mutagenicity.

Photosensitizers operate via two distinct mechanisms, termed Types 1 and 2. The type 1 mechanism is shown in the following scheme:

Type 1 mechanisms involve direct energy or electron transfer from the photosensitizer to the cellular components thereby causing cell death. Type 2 mechanisms involve two distinct steps, as shown in the following scheme:

In the first step, singlet oxygen is generated by energy transfer from the triplet excited state of the photosensitizer to the oxygen molecules surrounding the tissues. In the second step, collision of singlet oxygen with the tissues promotes tissue damage. In both Type 1 and Type 2 mechanisms, the photoreaction proceeds via the lowest triplet state of the sensitizer. Hence, a relatively long triplet lifetime is required for effective phototherapy. In contrast, a relatively short triplet lifetime is required to avoid photodamage to the tissue caused by photosensitizers.

The biological basis of tissue injury brought about by tumor phototherapeutic agents has been the subject of intensive study. Various reasonable biochemical mechanisms for tissue damage have been postulated even though the type and number of photosensitizers employed in these studies are relatively small. These biochemical mechanisms are as follows: a) cancer cells upregulate the expression of low density lipoprotein (LDL) receptors, and photodynamic therapy (PDT) agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Most of the currently known photosensitizers are commonly referred to as photodynamic therapy (PDT) agents and operate via the Type 2 mechanism. For example, Photofrin II (a hematoporphyrin derivative) has been recently approved by the United States Food and Drug Administration for the treatment of bladder, esophageal, and late-stage lung cancers. However, Photofrin II has been shown to have several drawbacks: a low molar absorptivity ($\epsilon$=3000 M$^{-1}$), a low singlet oxygen quantum yield ($\phi$=0.1), chemical heterogeneity, aggregation, and prolonged cutaneous photosensitivity. Hence, there has been considerable effort in developing safer and more effective photosensitizers for PDT which exhibit improved light absorbance properties, better clearance, and decreased skin photosensitivity compared to Photofrin II. These include monomeric porphyrin derivatives, corrins, cyanines, phthalocyanines, phenothiazines, rhodamines, hypocrellins, and the like. However, these phototherapeutic agents also mainly operate via the Type 2 mechanism.

Surprisingly, there has not been much attention directed at developing Type 1 phototherapeutic agents, despite the fact that the Type 1 mechanism appears to be inherently more efficient than the Type 2 mechanism. First, unlike Type 2, Type 1 photosensitizers do not require oxygen for causing cellular injury. Second, the Type 1 mechanism involves two steps (photoexcitation and direct energy transfer), whereas the Type 2 mechanism involves three steps (photoexcitation, singlet oxygen generation, and energy transfer). Furthermore, certain tumors have hypoxic regions, which renders the Type 2 mechanism ineffective. However, in spite of the drawbacks associated with the Type 2 mechanism, only a small number of compounds have been developed that operate through the Type 1 mechanism, e.g. anthracyline antitumor agents.

Thus, there is a need to develop effective phototherapeutic agents that operate via the Type 1 mechanism. Phototherapeutic efficacy can be further enhanced if the excited state photosensitizers can generate reactive intermediates such as free radicals, nitrenes, carbenes, and the like, which have much longer lifetimes than the excited chromophore and have been shown to cause considerable cell injury.

SUMMARY OF THE INVENTION

The present invention discloses novel aromatic sulfenates that react mainly by a type 1 mechanism for phototherapy of tumors and other lesions. More specifically, the present invention discloses sulfenates having the formula, wherein E is selected from the group consisting of somatostatin, heat sensitive bacterioendotoxin, neurotensin, bombesin, cholecystekinin, steroid, and carbohydrate receptor binding molecules, and dihydroxyindolecarboxylic acid. X is selected from the group consisting of —($R^5$)NOC—, —($R^5$)NOCCH$_2$O—, —($R^5$)NOCCH$_2$CH$_2$O—, and —HNC(=S)NH. $R^1$ to $R^5$ are independently selected from the group consisting of hydrogen, C1-C10 alkyl, C5-C10 aryl, C1-C10 polyhydroxyalkyl and C1-C10 polyalkoxyalkyl. Q is either a single bond or an alkenyl, aromatic, or heteroaromatic radical derived from a compound selected from the group consisting of olefins, benzenes, naphthalenes, naphthoquinones, fluorines, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines; and Ar is an aromatic or heteroaromatic radical derived from a compound selected from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

The present invention also discloses a method of performing a therapeutic procedure using the sulfenate compounds of the present invention. An effective amount of a sulfenate photosensitizer having the formula, is administered to a subject. E is selected from the group consisting of somatostatin, heat sensitive bacterioendotoxin, neurotensin, bombesin, cholesystekinin, steroid, and carbohydrate receptor binding molecules, and dihydroxyindolecarboxylic acid. X is selected from the group consisting of —($R^5$)NOC—, —($R^5$)NOCCH$_2$O—, —($R^5$)NOCCH$_2$CH$_2$O—, and —HNC(=S)NH, $R^1$ to $R^5$ are independently selected from the group consisting of hydrogen, C1-C10 alkyl, C5-C10 aryl, C1-C10 polyhydroxyalkyl, and C1-C10 polyalkoxyalkyl. Q is either a single bond or an alkenyl, aromatic, or heteroaromatic radical derived from a compound selected from the group consisting of olefins, benzenes, naphthalenes, naphthoquinones, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines; Ar is an aromatic or heteroaromatic radical derived a compound selected from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines. The photosensitizer is allowed to accumulate in target tissue which is exposed to light of wavelength between 300 and 950 nm with sufficient power and fluence rate to perform the phototherapeutic procedure. The photoexcitation of the aromatic chromophore effects rapid intramolecular energy transfer to the sulfenate group, resulting in bond rupture and the production of two reactive free radicals which cause cellular injury.

These and other advantages and embodiments of the inventive compounds and methods will be apparent in view of the following figures, description, and examples.

DETAILED DESCRIPTION OF THE INVENTION

The present invention discloses novel sulfenate derivatives and their bioconjugates for phototherapy of tumors and other lesions.

The compounds have the general formula, wherein E is either a hydrogen atom or is selected from the group consisting of antibodies, peptides, peptidomimetics, carbohydrates, glycomimetics, drugs, hormones, or nucleic acids; X is selected from the group consisting of —($R^5$)NOC—, —($R^5$)NOCCH$_2$O—, —($R^5$)NOCCH$_2$CH$_2$O—, —OCN($R^5$)—, —HNC(=S)NH—, and HNC(=O)NH—; Q is either a single bond or an alkenyl, aromatic, or heteroaromatic radical derived from a compound selected from the group consisting of olefins, benzenes, naphthalenes, naphthoquinones, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines; $R^1$ to $R^5$ are independently selected from the group consisting of hydrogen, C1-C10 alkyl, C5-C10 aryl, C1-C10 polyhydroxyalkyl, and C1-C10 polyalkoxyalkyl; and Ar is an aromatic or heteroaromatic radical derived from a compound selected from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines.

In one embodiment, sulfenates according to the present invention have the general formula shown above, wherein E is selected from the group consisting of somatostatin, heat sensitive bacterioendotoxin, neurotensin, bombesin, cholesystekinin, steroid, and carbohydrate receptor binding molecules, and dihydroxyindolecarboxylic acid; X is selected from the group consisting of —($R^5$)NOC—, —($R^5$)NOCCH$_2$O—, —($R^5$)NOCCH$_2$CH$_2$O—, and —HNC(=S)NH; Q is a single bond or an olefinic or aromatic radical derived from a compound selected from the group consisting of alkenes, benzenes, furans, pyrroles, imidazoles, oxazoles, thiophenes, anthraquinones, quinolines, isoquinolines, indoles, acridines, acridones, phenanthridines, xanthenes, xanthones, and anthacylines; $R^1$ to $R^5$ are independently selected from the group consisting of hydrogen, C1-C10 alkyl, C5-C10 aryl, and C1-C10 polyhydroxyalkyl; and Ar is an aromatic or heteroaromatic radical derived from a compound selected from the group consisting of benzenes, diphenylmethanes, fluorenes, anthraquinones, naphthacenediones, pyridines, quinolines, isoquinolines, indoles, acridines, acridones, phenanthridines, xanthenes, xanthones, and anthacylines.

In an alternative embodiment, sulfenates according to the present invention have the general formula shown above, wherein E is selected from the group consisting of somatostatin, heat sensitive bacterioendotoxin (ST), neurotensin, bombesin, cholesystekinin (CCK), steroid, and carbohydrate receptor binding molecules; X is —($R^5$)NOC—, and —($R^5$)NOCCH$_2$O—; Q is a single bond or is selected from the group consisting of benzenes, furans, pyrroles, oxazoles, acridines, acridones, xanthenes, xanthones, and anthracyclines; $R^1$ to $R^5$ are independently selected from the group consisting of hydrogen, and C1-C10 alkyl; and Ar is an aromatic or heteroaromatic radical derived from a compound selected from the group consisting of benzenes, diphenylmethanes, fluorenes, anthraquinones, naphthacenediones, pyridines, quinolines, indoles, acridines, acridones, phenanthridines, xanthenes, xanthones, and anthacyclines.

Figure 1:
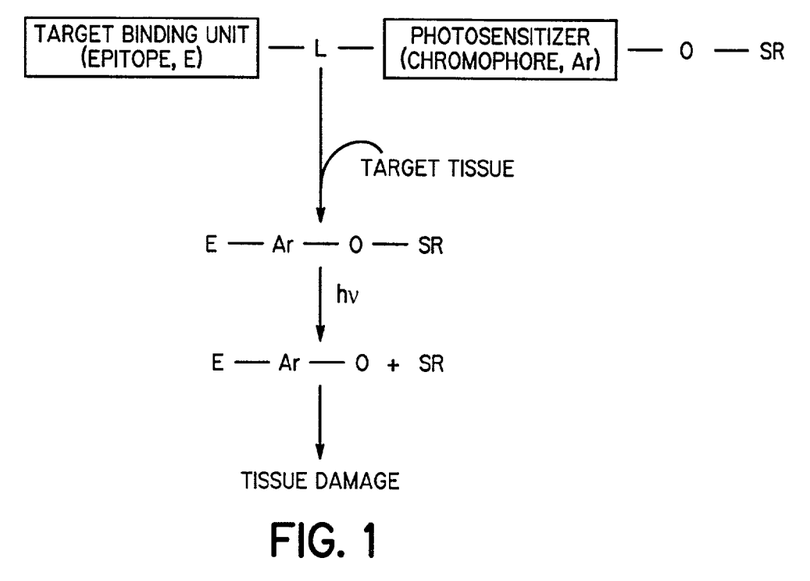
FIG. 1 is a schematic mechanism for activation of the inventive compounds.

These compounds operate mainly by a Type I mechanism as shown in FIG. 1, wherein —O—SR is the sulfenate moiety that produces free radicals upon photoactivation, and Ar is an aromatic chromophore that undergoes photosensitization. Aliphatic and aromatic sulfenates can be used for phototherapy, although aromatic sulfenates have better material handling properties, as is well known in the art (J. Amaudrut and O. Wiest, *The thermal sulfenate-sulfoxide rearrangement: A radical pair mechanism. Journal of the American Chemical Society*, 2000, 122, 3367-3374, which is expressly incorporated by reference herein in its entirety). L is a linker between the chromophore and the epitope. Epitope (E) is a particular region of the molecule that is recognized by, and binds to, the target site on the cell. An epitope is usually, but not always, associated with biomolecules which include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of biomolecules include steroid hormones for the treatment of breast and prostate lesions, somatostatin, bombesin, and neurotensin receptor binding molecules for the treatment of neuroendocrine tumors, cholecystekinin receptor binding molecules for the treatment of lung cancer; heat sensitive bacterioendotoxin (ST) receptor and carcinoembryonic antigen (CEA) binding molecules for the treatment of colorectal cancer, dihydroxyindolecarboxylic acid and other melanin producing biosynthetic intermediates for melanoma, integrin receptor and atheroscleratic plaque binding molecules for the treatment of vascular diseases, and amyloid plaque binding molecules for the treatment of brain lesions. Biomolecules for use in the present invention may also include synthetic polymers. Examples of synthetic polymers include polyaminoacids, polyols, polyamines, polyacids, oligonucleotides, aborols, dendrimers, and aptamers. Coupling of diagnostic and radiotherapeutic agents to biomolecules can be accomplished by methods well known in the art as disclosed in Hnatowich et al., *Radioactive Labeling of Antibody. A simple and efficient method. Science*, 1983, 220, 613-615; A. Pelegrin et al., *Photoimmunodiagnosis with antibody-fluorescein conjugates: in vitro and in vivo preclinical studies. Journal of Cellular Pharmacology*, 1992, 3,141-145; and U.S. Pat. No. 5,714,342, each of which are expressly incorporated by reference herein in their entirety. Successful specific targeting of fluorescent dyes to tumors using antibodies and peptides for diagnostic imaging of tumors has been demonstrated by us and others, for example, S. A. Achilefu et al., *Novel receptor-targeted fluorescent contrast agents for in vivo tumor imaging*, Investigative Radiology, 2000, 35(8), 479-485; B. Ballou et al., *Tumor labeling in vivo using cyanine-conjugated monoclonal antibodies*, Cancer Immunology and Immunotherapy, 1995, 41, 247-263; K. Licha et al., *New contrast agent for optical imaging: acid-cleavable conjugates of cyanine dyes with biomolecules*, In Biomedical Imaging: Reporters, Dyes, and Instrumentation, D. J. Bornhop, C. Contag, and E. M. Sevick-Muraca (Eds.), Proceedings of SPIE, 1999, 3600, 29-35, each of which are expressly incorporated by reference herein in their entirety. Therefore, the inventive receptor-targeted phototherapeutic agents are expected to be effective in the treatment of various lesions.

In the process outlined in FIG. 1, the photoexcitation of the aromatic chromophore effects rapid intramolecular energy transfer to the sulfenate group, resulting in bond rupture and production of two reactive free radicals which cause cellular injury.

For targeting purposes, external attachment of an epitope is used. If the aromatic sulfenate compounds themselves preferentially accumulate in the target tissue, however, an additional binding group may not be needed. For example, if Ar is an anthracycline moiety, it will bind to cancer cells directly and would not require an epitope for targeting purposes.

The synthesis of sulfenate derivatives is accomplished by the method disclosed in D. L. Pasto and F. Cottard, *Demonstration of the synthetic utility of the generation of alkoxy radicals by the photo-induced, homolytic dissociation of alkyl 4-nitrobenzenesulfenates*, Tetrahedron Letters, 1994, 35(25), 4303-4306, which is expressly incorporated by reference herein in its entirety. This method generally involves the condensation of sulfenyl chlorides with alcohols in the presence of an organic base. The sulfenate derivatives of the present invention contain additional functionalities that can be used to attach various types of biomolecules, synthetic polymers, and organized aggregates for selective delivery to various organs or tissues of interest.

Figure 2:
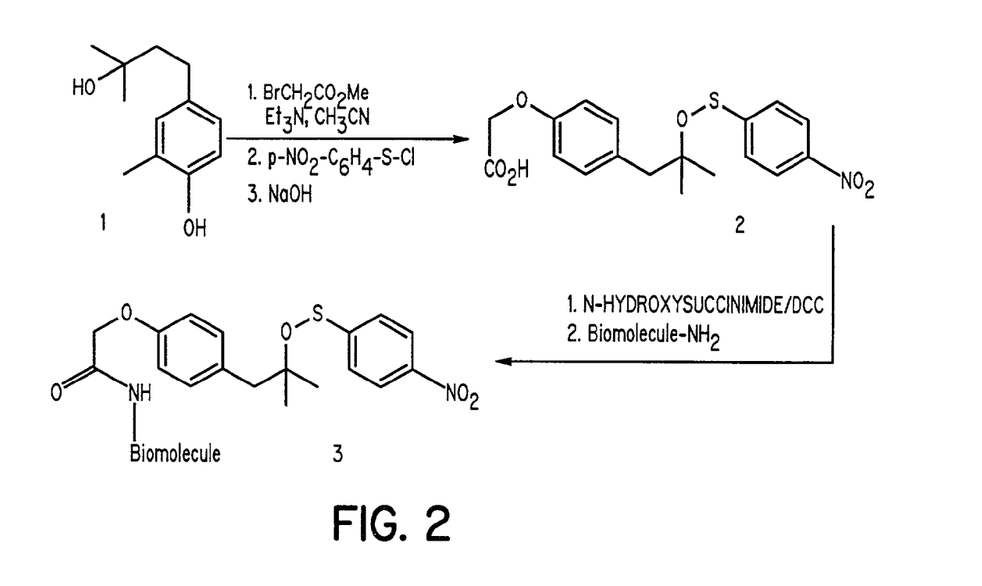
FIG. 2 is a schematic mechanism for the synthesis of a diol in accordance with the present invention.

A diol 1 is prepared by the reaction of methyl magnesium bromide with methyl 4-hydroxybenzoate. Referring to FIG. 2, alkylation of the resulting phenol with methyl bromoacetate, condensation of the tertiary alcohol with 4-nitrobenzenesulfenyl chloride, and saponification of the ester affords an intermediate acid 2. This acid 2 is then converted to the corresponding active ester using N-hydroxysuccimide (NHS) and dicyclohexylcarbodiimide (DCC). The active ester can be attached to any desired biomolecule of interest to form an aromatic sulfenate 3. Alternatively, the acid 2 can also be directly condensed with any biomolecule using automated peptide synthesizer. Specifically, the biomolecule of the present invention pertains to those binding to colorectal, cervical, ovarian, lung, and neuroendocrine tumors. These include somatostatin, cholesystekinin, bombesin, neuroendocrine, and ST receptor binding compounds.

Figure 3:
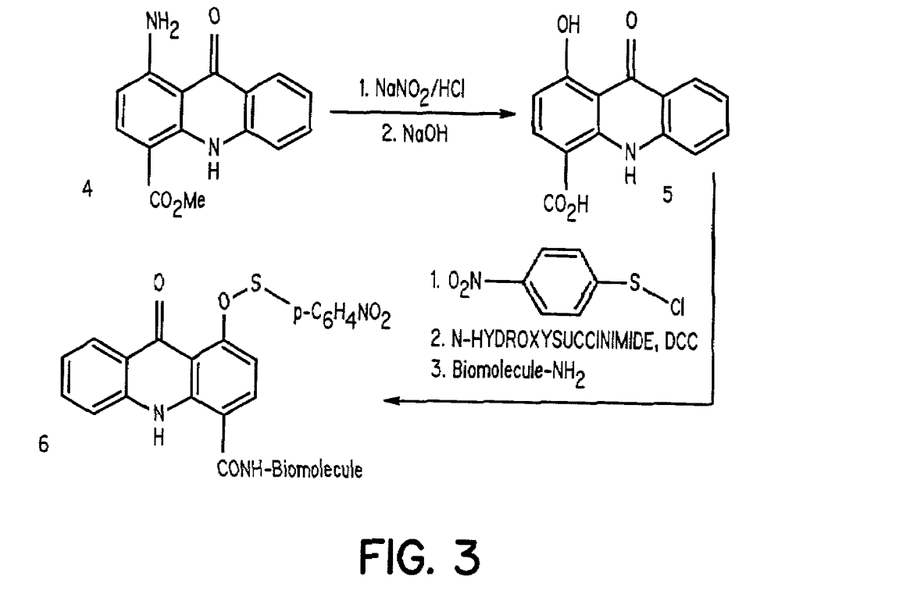
FIG. 3 is a schematic mechanism for the synthesis of an acridone derivative.

An acridone derivative is prepared according to FIG. 3. The starting material 4 is prepared according to a standard method known to one of skill in the art, as disclosed in K. Matsumura, 1-*Aminoacridine-4-carboxylic acid*., Journal of the American Chemical Society, 1938, 32, 591-592, which is expressly incorporated by reference herein in its entirety. An aminoacridone 4 is converted to a phenol by a standard method of diazotization of the amino group followed by displacement of the diazonium group with sodium hydroxide. The phenol 5 is converted to the corresponding p-nitrobenzenesulfenate and then conjugated to the biomolecules directly using an automated peptide synthesizer, or indirectly by the active ester route, to form the inventive acridine derivative 6.

Figure 4:
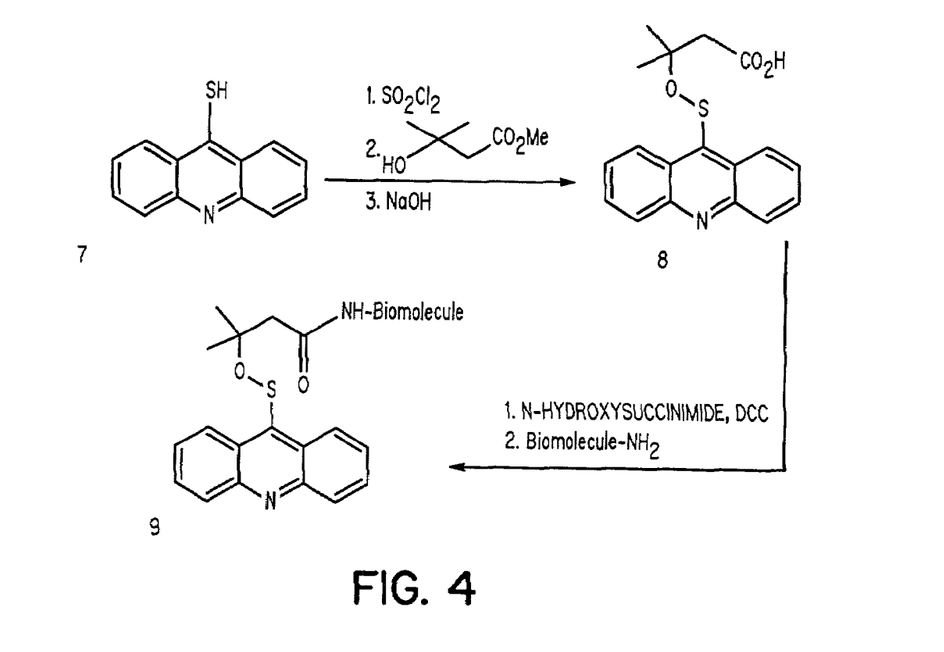
FIG. 4 is a schematic mechanism for the synthesis of an acridine sulfenate derivative.

A typical preparation of acridine-sulfenate derivative is outlined in FIG. 4. A thiol 7 is prepared from the known starting material 9-chloroacridone. It is converted to the corresponding sulfenyl chloride, condensed with methyl 3-hydroxy-3-methylbutyrate, and saponified to acid 8. The sulfenate-acid can be condensed with the desired biomolecules by the process previously described.

Figure 5:
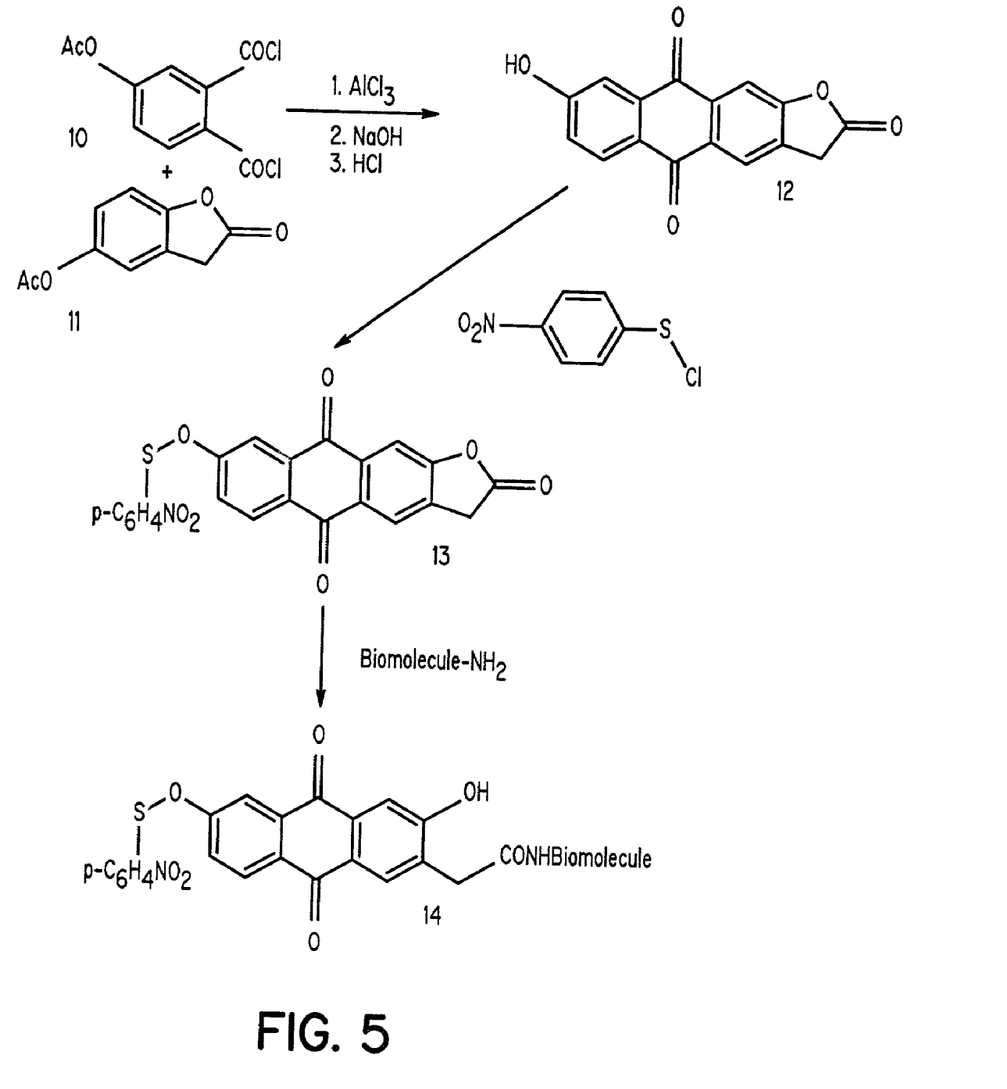
FIG. 5 is a schematic mechanism for the synthesis of an anthraquinone-sulfate derivative.

The anthraquinone-sulfenate derivatives can be synthesized according to FIG. 5. A diacid chloride 10 is reacted with a lactone 11 under Friedel-Crafts conditions followed by saponification to the corresponding hydroxyanthraquinone 12. It is then condensed with p-nitrobenzenesulfenyl chloride and conjugated to the desired biomolecule directly to form an inventive derivative 14. Alternatively, the lactone 10 could be hydrolyzed to the acid and then coupled to the biomolecule by conventional methods.

Figure 6:
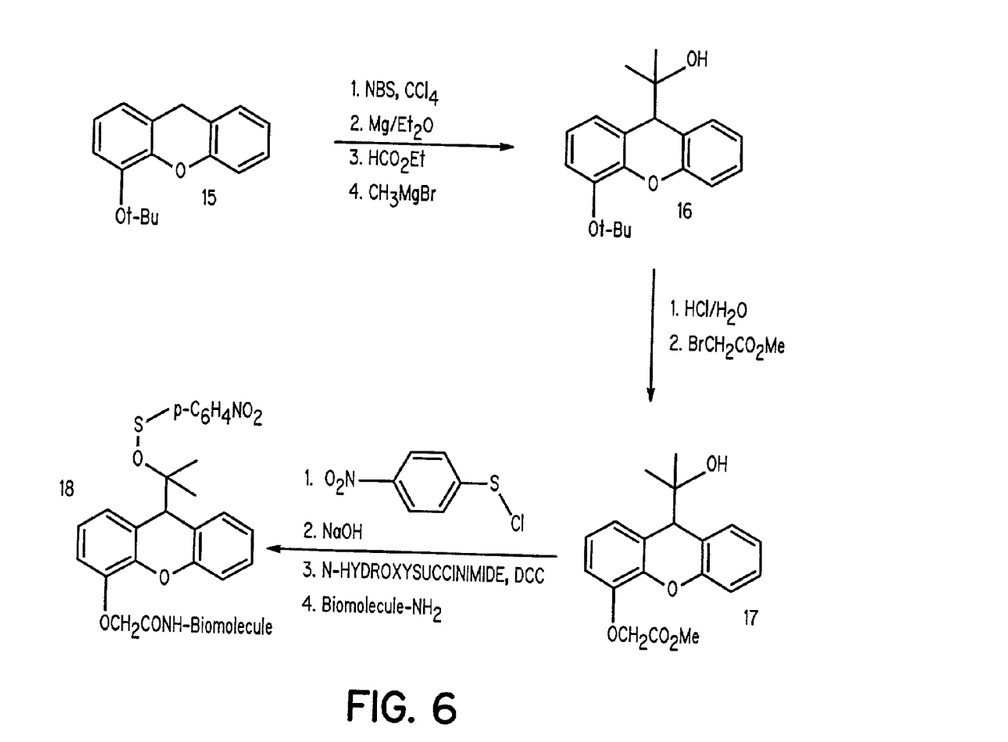
FIG. 6 is a schematic mechanism for the synthesis of a xanthene derivative.

The xanthene derivative can be prepared according to FIG. 6. A xanthone benzyl ether 15 is prepared from the known 4-hydroxyxanthone by alkylation with benzylbromide. The compound 15 was converted to the ether 16 in three steps: bromination, Grignard reaction with ethylformate, and Grignard reaction with methylmagnesium bromide. Deprotection of the t-butyl group with HCl followed by alkylation with methyl bromoacetate provides a tertiary alcohol 17. The tertiary alcohol 17 is then condensed with p-nitrobenzenesulfenyl chloride, saponified, and conjugated to the desired biomolecules mentioned previously.

Figure 7:
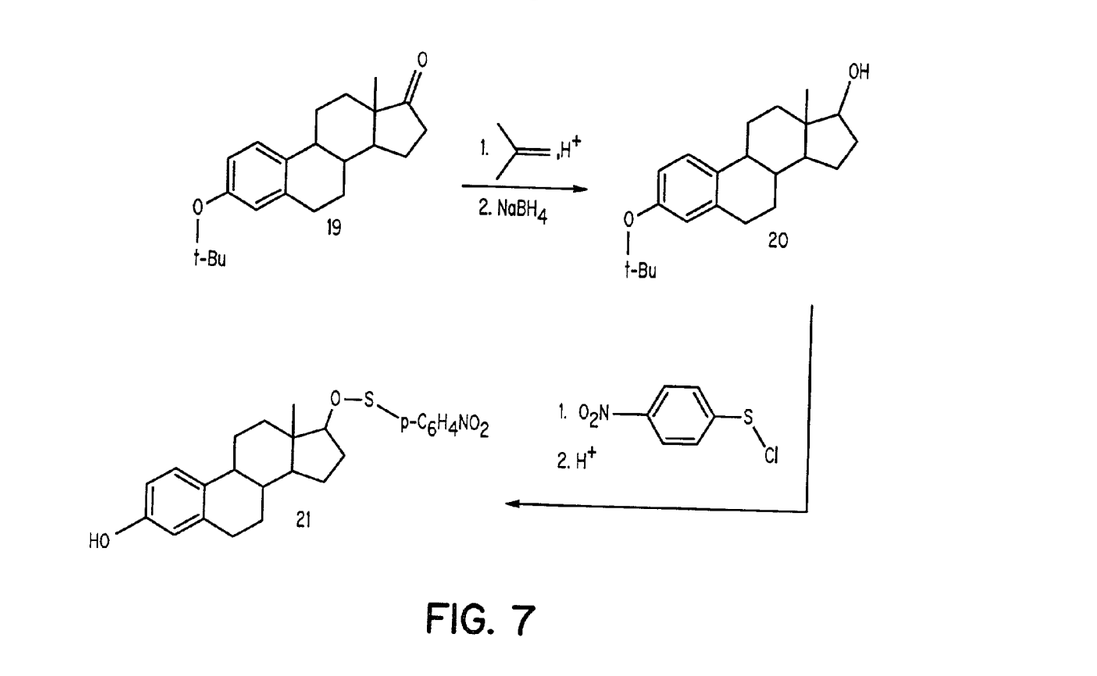
FIG. 7 is a schematic mechanism for the synthesis of a steroid-photosensitizer conjugate derivative.

The novel compositions of the present invention may vary widely depending on the contemplated application. For tumors, the biomolecule is selected from the class of tumor markers including, but not limited to, somatostatin, bombesin, neurotensin, cholesystekinin, heat sensitive bacterioendotoxin, estrogen, and progesterone receptor binding compounds. For vascular lesions, the biomolecule may be selected from the class of integrins, selecting, vascular endothelial growth factor, fibrins, tissue plasminogen activator, thrombin, LDL, HDL, Sialyl Lewis$^x$ and its mimics, and atherosclerotic plaque binding compounds. A typical synthetic scheme of a steroid-photosensitizer conjugate is shown in FIG. 7. Estrone is protected as the t-butyl ether 19 and reduced with sodium borohydride to a mono protected estradiol 20, which is then condensed with p-nitrobenzenesulfenyl chloride. Deprotection of the t-butyl group yields the steroid-photosensitizer conjugate 21.

Figure 8:
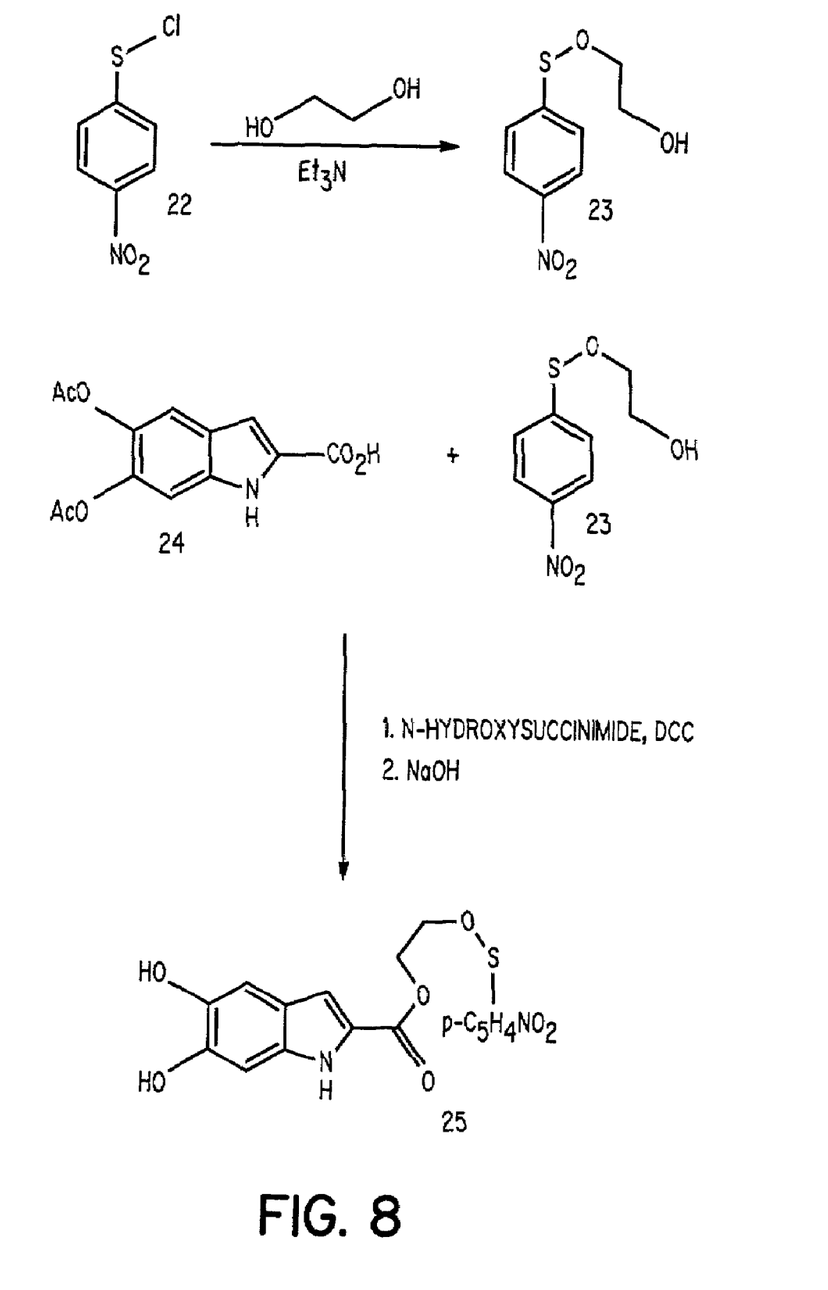
FIG. 8 is a schematic mechanism for delivering a photosensitizer to the site of a lesion by attaching it to a biosynthetic intermediate.

As previously described, some compounds accumulate in tumors or other lesions without the assistance of a bioactive carrier. Administration of δ-aminolevulinic acid, an intermediate in porphyrin biosynthesis, results in a two-fold uptake of porphyrins in tumors compared to normal tissues. Similarly, administration of dihydroxyindole-2-carboxylic acid, an intermediate in melanin biosynthesis, produces substantially enhanced levels of melanin in melanoma cells compared to normal cells. Thus, a photosensitizer may be delivered to the site of lesion by attaching it to a biosynthetic intermediate, as shown in FIG. 8. The mono sulfenate 23 is prepared by the reaction of p-nitrobenzenesulfenyl chloride 22 with ethylene glycol and is condensed with an indole derivative 24. Hydrolysis of the diacetate provides the conjugate 25.

Methods of performing therapeutic procedures with the inventive compounds are also disclosed. An effective amount of the inventive compounds in a pharmaceutically acceptable formulation is administered to a patient. For example, parenteral administration advantageously contains a sterile aqueous solution or suspension of the photosensitizer in a concentration ranging from about 1 nM to about 0.5 M. Preferred parenteral formulations have a concentration of 1 µM to 10 mM. Such solutions also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral compositions may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray. The dose of the photosensitizer may vary from 0.1 to 500 mg/kg body weight, preferably from 0.5 to 2 mg/kg body weight. The photosensitizer is allowed to accumulate in the region of interest, followed by illumination with light of wavelength 300 to 1200 nm, preferably 350 to 850 nm, at the site of the lesion. If the lesion is on the skin surface, the photosensitizer can be directly illuminated; otherwise, endoscopic catheters equipped with a light source may be employed to achieve phototherapeutic effect. The intensity, power, duration of illumination, and the wavelength of the light may vary widely depending on the location and site of the lesions. The wavelength of light may vary from 300 to 1200 nm. The fluence rate is preferably, but not always, kept below 200 mW/cm$^2$ to minimize thermal effects. Appropriate power depends on the size, depth, and the pathology of the lesion. The novel inventive compounds have broad clinical utility which includes, but is not limited to, phototherapy of tumors, inflammatory processes, and impaired vasculature.

The inventive compounds can be formulated into diagnostic or therapeutic compositions for enteral, parenteral, topical, or cutaneous administration. Topical or cutaneous delivery of the photosensitizer may also include aerosol formulation, creams, gels, solutions, etc. The compounds are administered in doses effective to achieve the desired diagnostic or therapeutic effect. Such doses may vary widely depending upon the particular complex employed, the organs or tissues to be examined, the equipment employed in the clinical procedure, the efficacy of the treatment achieved, and the like. These compositions contain an effective amount of the phototherapeutic agent along with conventional pharmaceutical carriers and excipients appropriate for the type of administration contemplated. These compositions may also include stabilizing agents and skin penetration enhancing agents.

The following example illustrates a specific embodiment of the invention pertaining to the preparation and properties of a typical bioconjugate derived from bombesin, a bioactive peptide, and a phototherapeutic molecule, sulfenate.

EXAMPLE

Synthesis of Sulfentate-bombesin (7-14) Conjugate

The peptide is prepared by fluorenylmethoxycarbonyl (Fmoc) solid phase peptide synthesis strategy with a commercial peptide synthesizer from Applied Biosystems (Model 432A SYNERGY Peptide Synthesizer). The first peptide cartridge contains Wang resin pre-loaded with an amide resin on 25 -µmole scale. The amino acid cartridges are placed on the peptide synthesizer and the product is synthesized from the C- to the N-terminal position. Coupling of the Fmoc-protected amino acids (75 µmol) to the resin-bound free terminal amine (25 µmol) is carried out with 2-(1H-benzotriazol-1-yl)-1,1,3,3-tetramethyluronium hexafluorophosphate (HBTU, 75 µmol)/N-hydroxybenzotriazole (HOBt, 75 µmol). Each Fmoc protecting group on the solid support was removed with 20% piperidine in dimethylformamide before the subsequent amino acid was coupled to it. The last cartridge contains sulfenate acid, which is coupled to the peptide automatically, thus avoiding the need for post-synthetic manipulations.

After the synthesis is completed, the product is cleaved from the solid support with a cleavage mixture containing trifluoroacetic acid (85%):water (5%):phenol (5%):thioanisole (5%) for 6 hours. The peptide-sulfenate conjugate is precipitated with t-butyl methyl ether and lyophilized in water:acetonitrile (2:3) mixture. The conjugate is purified by HPLC and analyzed with LC/MS. The sulfenate-bombesin (7-14) conjugate has the following molecular structure: p-azidotetrafluorobenzoyl-Gln-Trp-Ala-Val-Gly-His-Leu-Met-NH$_2$.

As would be apparent to skilled artisans, various changes and modifications are possible and are contemplated within the scope of the invention described. It should be understood that the embodiments of the present invention shown and described in the specification are only specific embodiments of the inventors who are skilled in the art and are not limiting in any way. Therefore, various changes, modifications or alterations to those embodiments may be made or resorted to without departing from the spirit of the invention and the scope of the following claims. The references cited are expressly incorporated by reference. For example, although the compositions of the present invention are primarily directed at therapy, most of the compounds containing polycyclic aromatic chromophores can also be used for optical diagnostic imaging purposes.

---

What is claimed is:

1. A method of performing a photosensitizing procedure which comprises the steps of:
   (a) topically administering to skin of a patient an effective amount of a sulfenate photosensitizer in a topical formulation with at least one excipient, the photosensitizer having the formula wherein E is dihyroxyindolecarboxylic acid;
   X is selected from the group consisting of —($R^5$)NOC—, —($R^5$)NOCCH$_2$O—, —($R^5$)NOCCH$_2$CH$_2$O—, and —HNC(=S)NH;
   $R^1$ to $R^5$ are independently selected from the group consisting of hydrogen, C1-C10 alkyl, C5-C10 aryl, C1-C10 polyhydroxyalkyl, and C1-C10 polyalkoxyalkyl;
   Q is either a single bond or an alkenyl, aromatic, or heteroaromatic radical derived from a compound selected from the group consisting of olefins, benzenes, naphthalenes, naphthoquinones, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines; and
   Ar is an aromatic or heteroaromatic radical derived from a compound selected from the group consisting of benzenes, naphthalenes, naphthoquinones, diphenylmethanes, fluorenes, anthracenes, anthraquinones, phenanthrenes, tetracenes, naphthacenediones, pyridines, quinolines, isoquinolines, indoles, isoindoles, pyrroles, imidiazoles, oxazoles, thiazoles, pyrazoles, pyrazines, purines, benzimidazoles, furans, benzofurans, dibenzofurans, carbazoles, acridines, acridones, phenanthridines, thiophenes, benzothiophenes, dibenzothiophenes, xanthenes, xanthones, flavones, coumarins, and anthacylines; and
   (b) exposing said skin with light of wavelength between 300 and 950 nm with sufficient power and fluence rate to activate the photosensitizer.

2. The method of claim 1 further comprising the step of allowing said photosensitizer to accumulate in said skin.

3. The method of claim 1, wherein X is selected from the group consisting of —($R^5$)NOC—, and —($R^5$)NOCCH$_2$O—; Q is a single bond; $R^1$ to $R^5$ are independently selected from the group consisting of hydrogen, C1-C10 alkyl, C5-C10 aryl, and C1-C10 polyhydroxyalkyl; and Ar is an aromatic radical derived from benzene.

4. The method of claim 1, wherein X is selected from the group consisting of —($R^5$)NOC—, and —($R^5$)NOCCH$_2$O—; Q is an alkenyl radical derived from olefins; $R^1$ to $R^5$ are independently selected from the group consisting of hydrogen, C1-C10 alkyl, C5-C10 aryl, and C1-C10 polyhydroxyalkyl; and Ar is an aromatic radical derived from benzene.

5. The method of claim 1, wherein X is selected from the group consisting of —($R^5$)NOC—, and —($R^5$)NOOCH$_2$O—; Q is an aromatic radical derived from a compound selected from the group consisting of benzenes, furans, pyrroles, imidazoles, thiophenes, anthraquinones, quinolines, indoles, acridines, acridones, xanthenes, xanthones, phenanthridines, and anthacylines; $R^1$ to $R^5$ are independently selected from the group consisting of hydrogen, C1-C10 alkyl, C5-C10 aryl, and C1-C10 polyhydroxyalkyl; and Ar is an aromatic radical derived from benzene.

6. The method of claim 1, wherein X is selected from the group consisting of —($R^5$)NOC—, and —($R^5$)NOCCH$_2$O—; Q is a single bond; $R^1$ to $R^5$ are independently selected from the group consisting of hydrogen, C1-C10 alkyl, C5-C10 aryl, and C1-C10 polyhydroxyalkyl; and Ar is an aromatic radical derived from anthracene.

7. The method of claim 1, wherein X is selected from the group consisting of —($R^5$)NOC—, and —($R^5$)NOCCH$_2$O—; Q is an alkenyl radical derived from olefins; R1 to $R^5$ are independently selected from the group consisting of hydrogen, C1-C10 alkyl, C5-C10 aryl, and C1-C10 polyhydroxyalkyl; and Ar is an aromatic radical derived from anthracene.

8. The method of claim 1, wherein X is selected from the group consisting of —($R^5$)NOC—, and —($R^5$)NOCCH$_2$O—; Q is an aromatic radical derived from a compound selected from the group consisting of benzenes, furans, pyrroles, imidazoles, thiophenes, anthraquinones, quinolines, indoles, acridines, acridones, xanthenes, xanthones, phenanthridines, and anthacylines; $R^1$ to $R^5$ are independently selected from the group consisting of hydrogen, C1-C10 alkyl, C5-C10 aryl, and C1-C10 polyhydroxyalkyl; and Ar is an aromatic radical derived from anthracene.

9. The method of claim 1, wherein X is selected from the group consisting of —($R^5$)NOC—, and —($R^5$)NOCCH$_2$O—; Q is a single bond; $R^1$ to $R^5$ are independently selected from the group consisting of hydrogen, C1-C10 alkyl, C5-C10 aryl, and C1-C10 polybydroxyalkyl; and Ar is an aromatic radical derived from acridine.

10. The method of claim 1, wherein X is selected from the group consisting of —($R^5$)NOC—, and —($R^5$)

NOCCH$_2$O—; Q is an alkenyl radical derived from olefins; R$^1$ to R$^5$ are independently selected from the group consisting of hydrogen, C1-C10 alkyl, C5-C10 aryl, and C1-C10 polyhydroxyalkyl; and Ar is an aromatic radical derived from acridine.

11. The method of claim 1, wherein X is selected from the group consisting of —(R$^5$)NOC—, and —(R$^5$)NOCCH$_2$O—; Q is an aromatic radical derived from a compound selected from the group consisting of benzenes, furans, pyrroles, imidazoles, thiophenes, anthraquinones, quinolines, indoles, acridines, acridones, xanthenes, xanthones, phenanthridines, and anthacylines; R$^1$ to R$^5$ are independently selected from the group consisting of hydrogen, C1-C10 alkyl, C5-C10 aryl, and C1-C10 polyhydroxyalkyl; and Ar is an aromatic radical derived from acridine.

12. The method of claim 1, wherein X is selected from the group consisting of —(R$^5$)NOC—, and —(R$^5$)NOCCH$_2$O—; Q is a single bond; R$^1$ to R$^5$ are independently selected from the group consisting of hydrogen, C1-C10 alkyl, C5-C10 aryl, and C1-C10 polyhydroxyalkyl; and Ar is an aromatic radical derived from phenanthridine.

13. The method of claim 1, wherein X is selected from the group consisting of —(R$^5$)NOC—, and —(R$^5$)NOCCH$_2$O—; Q is an alkenyl radical derived from olefins; R$^1$ to R$^5$ are independently selected from the group consisting of hydrogen, C1-C10 alkyl, C5-C10 aryl, and C1-C10 polyhydroxyalkyl; and Ar is an aromatic radical derived from phenanthridine.

14. The method of claim 1, wherein X is selected from the group consisting of —(R$^5$)NOC—, and —(R$^5$)NOCCH$_2$O—; Q is an aromatic radical derived from a compound selected from the group consisting of benzenes, furans, pyrroles, imidazoles, thiophenes, anthraquinones, quinolines, indoles, acridines, acridones, xanthenes, xanthones, phenanthridines, and anthacylines; R$^1$ to R$^5$ are independently selected from the group consisting of hydrogen, C1-C10 alkyl, C5-C10 aryl, and C1-C10 polyhydroxyalkyl; and Ar is an aromatic radical derived from phenanthridine.

15. The method of claim 1 wherein the sulfenate photosensitizer is topically administered to the skin in a formulation including the sulfenate photosensitizer and materials selected from the group consisting of liquid excipients and semisolid excipients.

16. The method of claim 1 wherein the sulfenate photosensitizer is administered in a form selected from the group consisting of an aerosol spray, a cream, a gel, and a solution.

17. The method of claim 1 wherein the sulfenate photosensitizer is administered to melanoma tissue.

* * * * *

UNITED STATES PATENT AND TRADEMARK OFFICE
CERTIFICATE OF CORRECTION

PATENT NO. : 7,235,685 B2
APPLICATION NO. : 09/898887
DATED : June 26, 2007
INVENTOR(S) : Raghavan Rajagopalan et al.

It is certified that error appears in the above-identified patent and that said Letters Patent is hereby corrected as shown below:

Claim 5, Line 29, Col. 12 - "$NOOCH_2O$" should read --$NOCCH_2O$--

Claim 7, Line 46, Col. 12 - "R1" should read --$R^1$--

Claim 9, Line 64, Col. 12 - "polybydroxyalkyl" should read --polyhydroxyalkyl--

Signed and Sealed this

Eighth Day of July, 2008

JON W. DUDAS
*Director of the United States Patent and Trademark Office*

SEQUENCE LISTING

<160> NUMBER OF SEQ ID NOS: 1

<210> SEQ ID NO 1
<211> LENGTH: 8

```
<212> TYPE: PRT
<213> ORGANISM: Artificial Sequence
<220> FEATURE:
<223> OTHER INFORMATION: The sulfenate-bombesin (7-14) conjugate has the
      following molecular structure:
      p-azidotetrafluorobenzoyl-Gln-Trp-Ala-Val-Gly-His-Leu-Met-NH2.

<400> SEQUENCE: 1

Gln Trp Ala Val Gly His Leu Met
1               5
```